United States Patent
Stelzer et al.

(10) Patent No.: US 6,309,345 B1
(45) Date of Patent: Oct. 30, 2001

(54) MINIMALLY INVASIVE SURGERY DEVICE

(76) Inventors: Paul Stelzer; Stuart Stelzer, both of 350 E. 79th St., Apt. 22D, New York, NY (US) 10021

( * ) Notice: Subject to any disclaimer, the term of this patent is extended or adjusted under 35 U.S.C. 154(b) by 0 days.

(21) Appl. No.: 09/247,707

(22) Filed: Feb. 9, 1999

Related U.S. Application Data

(63) Continuation-in-part of application No. 08/916,147, filed on Aug. 21, 1997, now Pat. No. 5,924,976.

(51) Int. Cl.[7] ............................. A61B 1/018; A61F 2/06
(52) U.S. Cl. ...................... 600/106; 600/104; 600/111; 600/116; 606/159; 606/194; 623/1.11
(58) Field of Search .................................... 600/106–108, 600/104, 116, 111, 166, 179, 175; 604/96, 101.1; 606/194, 1, 159, 108; 623/1.11

(56) References Cited

U.S. PATENT DOCUMENTS

| | | |
|---|---|---|
| 4,245,624 | 1/1981 | Komiya . |
| 4,419,987 | 12/1983 | Ogiu . |
| 4,674,501 | 6/1987 | Greenberg . |
| 4,737,142 | 4/1988 | Heckele . |
| 4,862,874 | 9/1989 | Kellner . |
| 4,982,015 | 1/1991 | Hibino et al. . |
| 5,152,277 | 10/1992 | Honda et al. . |
| 5,291,010 | 3/1994 | Tsuji . |
| 5,320,091 | 6/1994 | Grossi et al. . |
| 5,368,015 | 11/1994 | Wilk . |
| 5,478,318 | 12/1995 | Yoon . |
| 5,484,418 | 1/1996 | Quiachon et al. . |
| 5,494,483 | 2/1996 | Adair . |
| 5,520,678 | * 5/1996 | Heckele ................................... 606/1 |
| 5,558,619 | 9/1996 | Kami et al. . |
| 5,603,687 | 2/1997 | Hori et al. . |
| 5,632,717 | * 5/1997 | Yoon ..................................... 600/106 |
| 5,762,603 | * 6/1998 | Thompson ............................ 600/122 |
| 5,879,288 | * 3/1999 | Suzuki et al. ......................... 600/156 |
| 5,928,193 | * 7/1999 | Campbell ............................... 604/96 |
| 6,066,090 | * 5/2000 | Yoon ..................................... 600/146 |
| 6,099,464 | * 8/2000 | Shimizu et al. ...................... 600/114 |

FOREIGN PATENT DOCUMENTS

WO 93/25138    12/1993   (WO) .

* cited by examiner

Primary Examiner—John P. Leubecker
(74) Attorney, Agent, or Firm—Frommer Lawrence & Haug; Matthew K. Ryan

(57) ABSTRACT

A surgical instrument comprising a node rotatably mounted within a restraining structure at the distal end of a shaft. The node can be rotated allowing manipulation and orientation of a surgical tool extending from the node at the distal end of the shaft through control remote from the distal end of the shaft. Cameras may also be located at the distal end of the shaft allowing stereoscopic imaging to be conveyed to an operator.

21 Claims, 13 Drawing Sheets

MINIMALLY INVASIVE SURGERY DEVICE

RELATED APPLICATIONS

This application is a continuation-in-part of allowed U.S. application Ser. No. 08/916,147 filed Aug. 21, 1997, now U.S. Pat. No. 5,924,976, which is incorporated herein by reference. All public documents referred to herein are likewise incorporated by reference.

FIELD OF THE INVENTION

The present invention relates to the field of minimally invasive or endoscopic surgical instruments, and more particularly, to an endoscopic instrument designed to allow improved instrument control and orientation, and to allow improved visual contact with the surgical area.

BACKGROUND OF THE INVENTION

Minimally invasive surgery techniques have become increasingly popular due to the rapid healing and greater efficiency provided by such techniques. As these techniques have been developed, workers and surgeons have been faced with the problem of working in small places not visible by direct line of sight. Various tools have been designed to deal with this problem although none has been entirely satisfactory.

The standard surgical approach has been to make a large enough opening in an anatomically suitable location (which will heal without functional impairment) to establish direct visualization. Magnification can then be used to enlarge the target structure and various fiberoptic light delivery systems can be used to illuminate it. The actual surgical manipulation is then performed by direct manipulation of instruments held in the surgeons' hands.

Various scopes have been devised to see into deeper structures of the body such as the trachea, esophagus, rectum, and bladder. These scopes were rigid tubes of appropriate size to fit a naturally-occurring orifice. Some were equipped with magnifying lenses and others used removable telescopes with direct or even angled viewing capability. The advent of fiberoptic technology revolutionized endoscopic tools by allowing them to be flexible, thus opening the entire colon and upper gastrointestinal tract to visualization and making the majority of the bronchial tree accessible under topical anesthesia.

Early in the history of endoscopy, gynecologists developed laparoscopic tools for diagnostic and then therapeutic work in the pelvis. This involved placing a rigid tube with a TV camera into the abdomen through the umbilicus after distending the abdominal cavity with carbon dioxide. Through separate small ports additional instruments could be inserted for manipulating various structures and performing tasks such as tubal ligation. This basic concept has now been radically expanded to allow laparoscopic removal of the gallbladder, appendix, or even kidney. In the chest, lung biopsies, vagotomy, pericardial windows, and even lobectomy can be performed with video-assisted thoracic surgery ("VATS").

The common feature of these prior endoscopic surgical techniques is that a camera is inserted at one point and tools are inserted at two or more other points. Traditionally, one person operates the camera, another uses retracting or holding tools, and the surgeon's hands are then free to dissect, cut, excise, ligate, clip and otherwise manipulate the target structure. The instruments used have tended to be very long and thin in order to extend deep within the body without making a large incision. The control, operation, orientation and manipulation of the tool is accomplished at the proximal end of the shaft by the operator. It is much akin to using two-foot long chopsticks in each hand to manipulate grapes at the bottom of a bottle with vision limited to a two-dimensional TV image controlled by someone else.

Other workers in this field have developed or suggested various tools to deal with these problems, although the shortcomings of each has prevented widespread use.

For example, several references have suggested a single endoscopic surgery device containing a camera device, light delivery means, and one or more shafts for the insertion of tools, such as forceps or a scalpel. The purpose of these devices was to overcome the difficulties caused by poor visualization and the awkward operation caused by the Separation of control of the camera and the working tool. In each of these devices, the manipulation and orientation of tools has been accomplished at the proximal end of the shaft by inserting or retracting the tool in the shaft, and by mechanisms to control the bending of the shaft. A device incorporating a single telescope with a channel for a working tool is disclosed in U.S. Pat. No. 5,320,091, and a similar device incorporating a CCD chip imaging device is disclosed in U.S. Pat. No. 5,291,010. U.S. Pat. No. 4,674,501 has suggested a device that would allow rotation of a surgical tool, with detent means to fix the position of the tool for use. This device, however, would allow only circular rotation of the tool, and does not allow for manipulation and orientation of the tool at the distal end of the shaft. The above devices have been problematic because the visual contact with the surgery location has been inadequate, further compounded by difficulties in the manipulation and orientation of the tools. Moreover, the use of a single camera has resulted in a lack of depth perception.

In another reference, U.S. Pat. No. 5,368,015, a system is suggested that uses two cameras to provide a stereoscopic image for use in a traditional system that uses multiple insertions to insert the camera and tools.

The human vascular system, particularly the arterial side, is frequently afflicted by the obstructive consequences of atherosclerosis. This results in decrease of blood flow through the vessel and subsequent ischemia (lack of oxygen) in the tissues served by this vessel. The most-frequently involved vessels are the iliac branches of the aorta and their distal ramifications, the femoral arteries. The aorta itself can also be severely affected in some patients. The carotid arteries in the neck are another common area for this kind of obstructive disease which causes decreased blood flow to the brain with serious stroke as the ultimate threat.

The standard approach to this kind of obstructive disease has been endarterectomy (opening the vessel and removing the entire inner lining (intima) along with the intraluminal disease and then closing the outer lining of the vessel). When the abdominal aorta and/or iliac vessels are involved, a vascular bypass graft is often constructed as an alternative. Earlier stages of disease may be approached with angioplasty balloon catheters with or without endovascular stents. These techniques have depended on radiographic imaging modalities to localize the disease and the deployment of therapeutic devices. The hazard of embolization of atherosclerotic debris downstream in the treated vessel raises the risk of serious injury to the very structures one is trying to protect.

In a typical manual endarterectomy, an opening is made in the body to allow the surgeon access to the subject artery (or in some instances vein). The surgeon then makes a lateral incision in the artery wall, penetrating through the wall, the lining and the hardened matter within the artery. The surgeon then manually separates the artery wall from the hardened matter or plaque, ideally in such a way as to remove the matter in as large pieces as possible. Due to the consistency of the matter it is frequently possible to remove segments of hardened material as long as 10 cm through the opening. The artery is then sewn closed, and the body opening is likewise closed. The drawbacks to this process are that the patient is usually under general anesthesia, major trauma can be caused by the substantial body opening, only a limited portion of a limited number of arteries can be reached by direct incision, and the surgeon is unable to see the distal area where the plaque breaks.

Direct visualization of the inside of blood vessels has been made possible by the development of angioscopes—specialized flexible catheters with fiber optic equipment designed to provide a single camera-eye view of a vessel. There have also been contributions from intravascular ultrasound catheters which provide an internal view of a vessel with sound-wave technology. The ultrasound has the advantage of "seeing" through the blood stream, where the visible light spectrum devices demand a clear field. Neither of these devices is of any use in a totally occluded vessel.

It would therefore be of great advantage to have a new tool which would essentially treat the vascular tree as a body cavity of a specialized nature and transport appropriate tools through that tree to the point of obstruction and allow remote surgical treatment of the problem from the inside. The device would ideally allow for dissection of an endarterectomy plane, removal of debris, temporary occlusion of the vessel, irrigation, and suction, under stereoscopic visualization. In one embodiment, the working end of the remote dissector is modified to allow a port large enough for removal of bulky debris and the placement of two nodes at the tip, one for grabbing and or holding, the other for dissecting the tissue. Alternatively, the nodes could be incorporated into a smaller catheter to be passed through the outer catheter while the cameras, light sources, and irrigation equipment would be kept at the top along with a spatula and carbon dioxide insufflation nozzle. This brings the advantages of depth perception and control of instruments at the tip of the device to bear on the intravascular pathology.

It, therefore, has been found desirable to provide an endoscopic surgery device that allows for the manipulation and orientation of surgical tools at the distal end of the inserted shaft. It has also been found desirable to provide a camera for use in minimally invasive surgery, which solves the visual difficulties presented by prior devices, by providing stereoscopic vision through the use of two cameras placed at a proper distance for focus on the desired surgical area, combined in a single device with a surgical tool. It has further been found desirable to provide a single endoscopic surgery device incorporating stereoscopic vision in combination with a mechanism for allowing manipulation and orientation of surgical tools at the distal end of the device. It has further been found desirable to cofigure any of the devices for the conditions and requirements of intravascular surgery.

OBJECTS OF THE INVENTION

It is an object of the present invention to provide an endoscopic surgery tool that allows for the manipulation and orientation of a surgical tool at the distal end of an inserted shaft. It is also an object of the present invention to provide for stereoscopic viewing of the surgical area through the use of at least two properly spaced cameras, combined in a single device with at least one surgical tool. It is a further object of the present invention to provide a single device that incorporates stereoscopic vision using plural cameras and incorporates at least one surgical tool that can be manipulated and oriented at the distal end of an inserted shaft. It is a further object to provide a single device that incorporates stereoscopic vision using plural cameras and incorporates at least one surgical tool that can be manipulated and oriented at the distal end of an inserted shaft, which includes appropriate channels for delivering fluids or other substances (which may have pharmaceutical or biologically active properties) to a desired location that is or may be inaccessible from outside the body. It is another object of the present invention to provide for tools specifically designed for use in a nodal system for use at the distal end of a shaft. It is another object of the present invention to provide a device specifically configured for intravascular surgery.

SUMMARY OF THE INVENTION

The present invention relates to an endoscopic surgery device that allows for control of surgical tools at the distal end of a shaft, through the use of a rotating node structure. The invention also relates to an endoscopic surgery device which provides for stereoscopic viewing of the surgical area through at least two cameras incorporated into a single device with one or more tools for performing surgical functions. The invention further relates to a single endoscopic surgery device incorporating stereoscopic vision and distal-end control of surgical tools.

To achieve these advantageous features of the present invention, there is provided an instrument comprising a node at the distal end of a shaft, wherein a surgical tool can be inserted through the node and the node can be rotated allowing manipulation and orientation of the surgical tool at the distal end of the shaft through control remote from the distal end of the shaft. Further, there is provided a particular node structure at the distal end of the device which, through control remote from the distal end of the device, can rotate a surgical tool in the (X) and (Y) dimensions, and allows for the movement of the tool in the (Z) dimension. There further is provided at least two cameras configured such that at the appropriate distance from the device, the surgical area will appear to the operator in stereoscopic vision. There is also provided an instrument comprising (i) a node at the distal end of a shaft, wherein a tool can be inserted through the node allowing manipulation and orientation of the tool at the distal end of the shaft through control remote from the distal end of the shaft, (ii) a plurality of cameras located at the distal end of the shaft positioned so that they can convey a stereoscopic image to an operator; and (iii) a light source.

There is also provided a specific embodiment that is configured to allow intravascular surgical procedures, such as dissection of an endarterectomy plane, removal of debris, temporary occlusion of the vessel, irrigation and suction.

Further, there is provided a flexible shaft housing providing for ports for all necessary or desired tools and accessories, which can include the aforementioned cameras, one or more light sources, channels for suction and fluid flow, and one or more, preferably at least two channels, ending in nodes for introducing tools such as forceps, scissors, a cautery tool, or other commonly used surgical instruments. There is further provided a variety of surgical tools specially designed for use in conjunction with the node control mechanism.

DETAILED DESCRIPTION OF THE PREFERRED EMBODIMENTS

Figure 1:
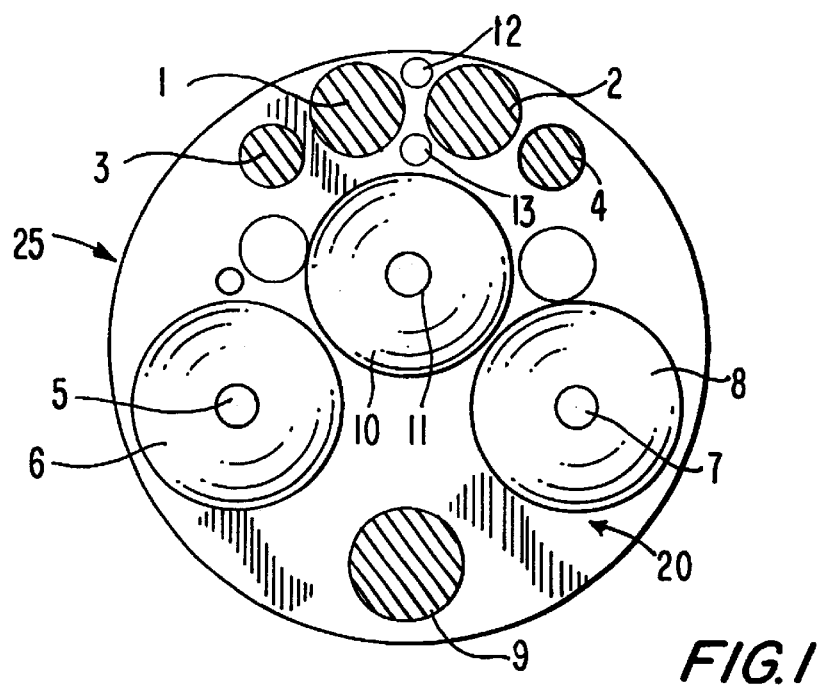
FIG. 1 shows an end view of a preferred embodiment of the invention.

FIG. 1 shows an end view of the configuration of one of the preferred embodiments. RGB chip camera units 1 and 2 are positioned to the right and left of the center axis of the shaft, and are spaced such that the targeted area will be within the focal distance of the cameras so that a stereoscopic image of the surgical area can be produced. Light is provided by fiber optic sources 3 and 4. Three nodes (6, 8 and 10) are located below the cameras, and each node has a tool port at its center (5, 7 and 11). A balloon port (9) may optionally be used. Sources for $H_2O$ and $CO_2$ are shown at 12 and 13. The selection of the number of tools, nodes, ports and other mechanisms may vary depending on the nature of the surgery to be performed.

A protective plate, 20, is placed over the distal end of the catheter, 25, with openings for all desired ports and nodes. The plate is fastened to the outer surface of the catheter, and provides both support for the distal end of the various ports and protection against contamination of the interior of the device by undesired substances, such as blood or other fluids, which can foul the operation of the sensitive mechanisms involved. The distal ends of the various ports may be fastened to the protective plate for support, and to prevent movement. It is preferred that the node shafts be permitted to move in and out relative to the protective plate, however, to permit more flexibility of tool operation, to allow the tool operation and location to be adjusted within the field of vision provided by the cameras, and to allow the frame of reference of the operator, provided by the cameras, to remain constant relative to the moving tools.

The camera system used can be varied according to available technology. Suitable camera systems are disclosed in U.S. Pat. No. 5,291,010 and the references discussed therein.

Figure 2:
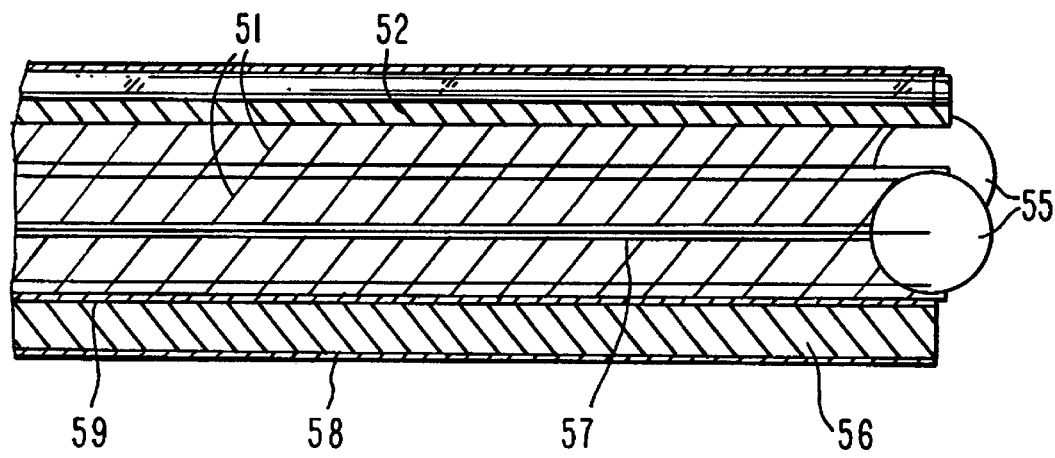
FIG. 2 shows a cut-out side view of the same embodiment shown in FIG. 1.

FIG. 2 shows a cut-out side view of an embodiment as in FIG. 1. The shafts for the nodes can be seen, 51, as can the lines for the fiber optic light sources 52 and the RGB cameras, Two nodes appear, 55, which are shown connected to a tool shaft, 57, and to control lines 59. A balloon shaft, 56, is also shown. All are contained within the external catheter housing, 58. In currently available devices, it is known how to control the bending of the flexible shaft housing to position the end of the shaft, and how to lock the shaft into place to prevent undesired movement.

A preferred embodiment combines the imaging vehicle and a mechanism for manipulating tools at the distal end of the device into a single system controlled by a single operator. The operator or surgeon introduces a flexible tubular structure which contains two cameras (for true stereoscopic vision), primary and secondary working tools, and electronic (robotic) control systems. This allows for the restoration of classical hand-eye coordination in a virtual reality-type environment. Two separate screens display the video image (one for each eye) and motion and action of the dissector's primary and secondary tools is controlled by the surgeon's hands. The control devices are in the familiar shape of commonly used tools such as forceps and cautery wand. The entire device is introduced into the appropriate body cavity through a stabilizing port which in turn is inserted through a small strategically-located incision, much as the current endoscopic camera is inserted.

The stereoscopic vision can be provided by a number of means, but in the preferred embodiment is accomplished by a dual light source and RGB camera chip system set up on either side of the nodes and connected to a heads-up display system projected independently into the surgeon's eyepieces or into the two sides of a stereoscopic viewing visor.

The distance between the cameras should be such that the surgical area can be brought into focus of the operator. In the preferred orientation, the ratio of the distance between the cameras to the distance to the surgical area is approximately $3/18$. For example, to work on an area 3.6 cm from the camera system, the cameras should be placed approximately 6 mm apart for the best comfort of the operator.

Alternatively, the images from the cameras can be transferred to a microprocessor and manipulated by appropriate imaging software to produce a computer-generated three-dimensional image of the surgical area, which can be displayed on a standard monitor. As yet another alternative, the cameras can be mounted on nodes as discussed below to provide an increased range of vision. It is expected that the best available focusing and other imaging technology will be used. There is no reason that the light/camera pair be limited to the visible light range, but any suitable electromagnetic radiation may be used, including xray, ultraviolet, infrared, or radiation of a specific desired wavelength or wavelengths. Particularly, where the environment is expected to involve blood or another bodily fluid, the wavelength may be selected so that the fluid provides the least vision obstruction.

Depending on the type of surgery, a single surgeon dissector can be used which would have capabilities for clip application, scissors, or suction/irrigation in the auxiliary right hand port. The left-hand port is typically used for forceps according to traditional surgical practices. The primary port may be used for a dissection/cautery wand.

For more complex procedures, an assistant dissector can be used, much as a surgeon uses a first assistant. The assistant dissector can be equipped with a retractor blade in the primary port, forceps in the left-hand port, and suction/irrigation in the right-hand auxiliary port.

In one particular embodiment, the unit consists of the sterile semi-flexible shaft housing with an external diameter of approximately 2.0 cm. The distal end houses the working ports with the node for each. The shaft itself is largely hollow to allow room for the individual working tool shafts, control wires, fiberoptic light cables, and electronic system cable. The housing is much like a flexible endoscope with control cabling to allow basic device orientation and introduction into the body. Control of the bending of the shaft may also be accomplished using automated means, such as that disclosed in U.S. Pat. No. 4,982,725. The proximal end of the housing is the electrical/mechanical interface for controlling instruments. Rotation and depth of insertion are controlled at the proximal end. The angle of tool orientation is controlled at the node level, moved by a pair of X and pair of Y axis cables for each node connected to the proximal interface gear. Optionally, the device may contain a changer and additional surgical tools within the shaft, such that the tools can be switched during use without withdrawal from the shaft, or without access to the distal end of the shaft.

In addition, it may be desirable to administer pharmaceutical or biologically active compounds or substances to one or more specific desired locations within the body. This may be desirable because the desired location is inaccessible, or not easily accessible by typical means such as digestion, injection, suppository, salve, etc. In addition the substance may have undesired toxic effects, such as renal or hepatic toxicity, if administered in large doses, and direct administration to a specific desired location may minimize dosing requirements and minimize exposure to sensitive body tissues and organs. In other instances, such as may be common in the field of biotechnology, the substance is simply very expensive, and direct administration to a specific desired location may minimize costs. Or the substance may be designed to dissolve, aid in dissolution, or otherwise chemically affect the target area.

Where any of these situations occurs, a device may be configured to provide a channel within an outer catheter for administering a pharmaceutical or biologically active substance to the distal end of the catheter. The distal end of this catheter may be left open, or may be a needle for injecting the desired substance, or may be a nozzle for controlling the flow and/or direction of the substance. Such a channel could also be used to administer glue for connecting tissue or plugging holes. The catheter may be flexible or may be any of the types of shafts discussed in this application. The catheter may also include one or more nodes, and may also include stereoscopic vision with an appropriate vision system as discussed herein. A specific area within the body can then be treated by administering a substance through the catheter so configured.

Figure 3:
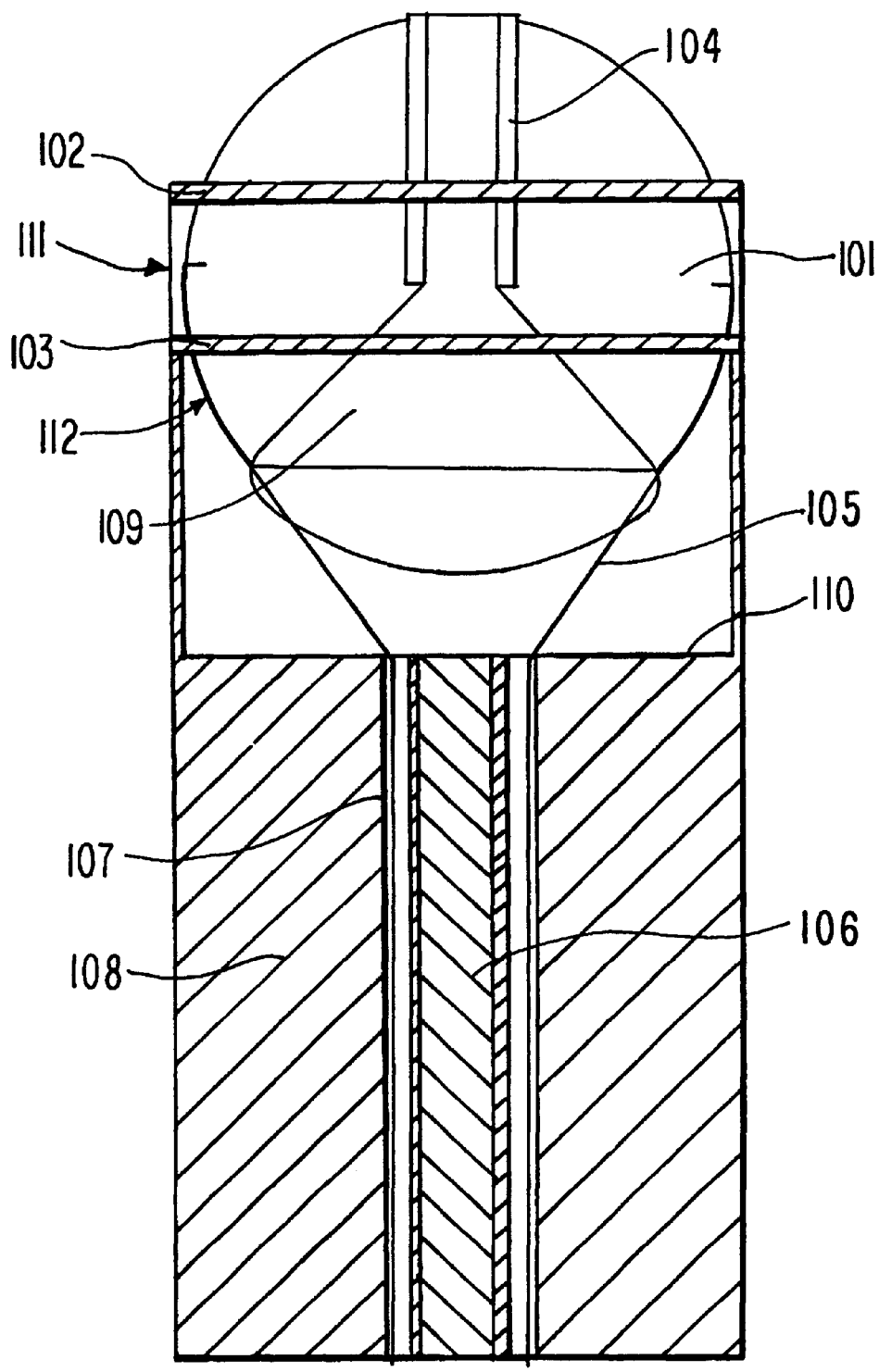
FIG. 3 is a diagram showing an individual node and port unit.

FIG. 3 shows a preferred configuration of a single node with accompanying support and control mechanisms. The node, 101, is positioned at the end of a shaft, 108, constrained by braces, 102 and 103. The braces are positioned above and below the center or "equator" of the node and at points where the circumference is smaller so that the braces can provide adequate support for the node, preventing it from either being pushed outward through the outer brace, 102, or compressed inward through the inner brace, 103. The internal radius of the braces should correspond to the diameter of the node at that point, and the inner surface of the brace is preferably beveled to allow rotation of the node with the least possible resistance, while providing all necessary support. The outer edge of the brace is fastened to the wall of the node shaft. The diameter (D) of the inner edge of the brace can be calculated according to the formula $D=2\sqrt{(r^2-(x/2)^2)}$, where r is the radius of the node and x is the distance between the braces. This calculation assumes that the braces are placed symmetrically about the center circumference (i.e., the equator), of the node and that the node is spherical. If a different shape or configuration is used, the dimensions can be calculated according to well-known geometric principles. Alternatively, instead of two separate braces, a unitary fused socket can be used for support. The socket can be fabricated to conform to the outer contour of the node providing support along the entire surface of the socket.

A tool shaft provides for connection of the tool (not shown) with the operator controls. The tool shaft, 106, and four shafts, generally designated 107, for the control lines are fastened to a third brace, 110, which is affixed to the wall of the node shaft. When not in use, the tool resides in the tool port, 104 and the mechanical or electrical control lines for the actuation and operation of the tool are connected to the control panel through the tool shaft, 106.

The posterior opening of the node, 109, is open to allow control of the tool when the node is rotated during use. The anterior opening of the node, 104, is preferably narrower to provide support and direction for the tool when it is inserted through the node for use.

The positioning and orientation of the node are accomplished using control lines, 105. The control lines are positioned so that by varying the tension on the control lines through the shaft, 107, the orientation of the node can be controlled in any direction. In the preferred embodiment, the control lines are attached to the node through connectors located at or above the equator of the node, and the node is fabricated with grooves, 112, and connector elements, 111, for guiding and connecting the control lines. Other means of changing the orientation of the node can be used, such as motor drives or magnetic means.

Figure 13:
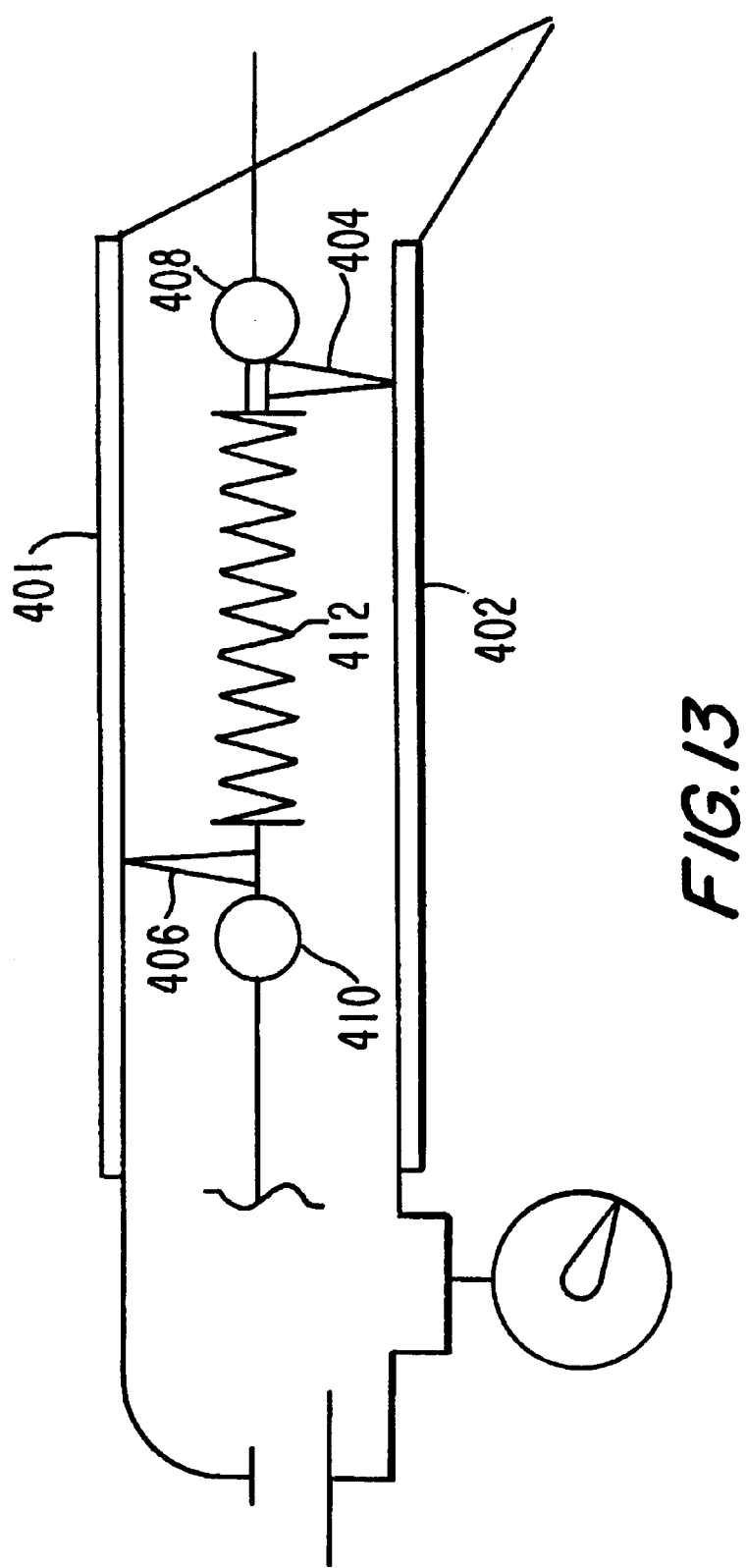
FIG. 13 shows a tension measurement device to provide tactile feedback to an operator.

The node is preferably a substantially spherical housing with a central passage for the shaft of each instrument. The three-dimensional orientation is determined by movement of the sphere in two planes and movement of the shaft in the third. The back of the node is preferably open to allow free motion of the shaft. The entire shaft may also rotate, or be fitted with a rotation-permitting device such as a bearing, to allow complete control of the positioning of the instruments. One such rotational device is disclosed in U.S. Pat. No. 4,674,501. In another embodiment, the sleeves in which the shaft moves may be equipped with pressure-sensitive material to transduce tissue resistance for tactile perception. Such materials undergo changes in electrical resistance corresponding to the stress of the material. This change in electrical resistance can be measured, and converted into resistance that the operator feels in operating the tool. Such an arrangement is shown in FIG. 13. Additional flexibility can be provided if the node and its controls are configured so that the tool can spin about the (z) axis extending through its center outward from the shaft.

As another alternative, the tool and node can be fused together, or can be fabricated as a unitary structure, which provides certain benefits, although it does not allow for the tool to be switched apart from the node.

Figure 4:
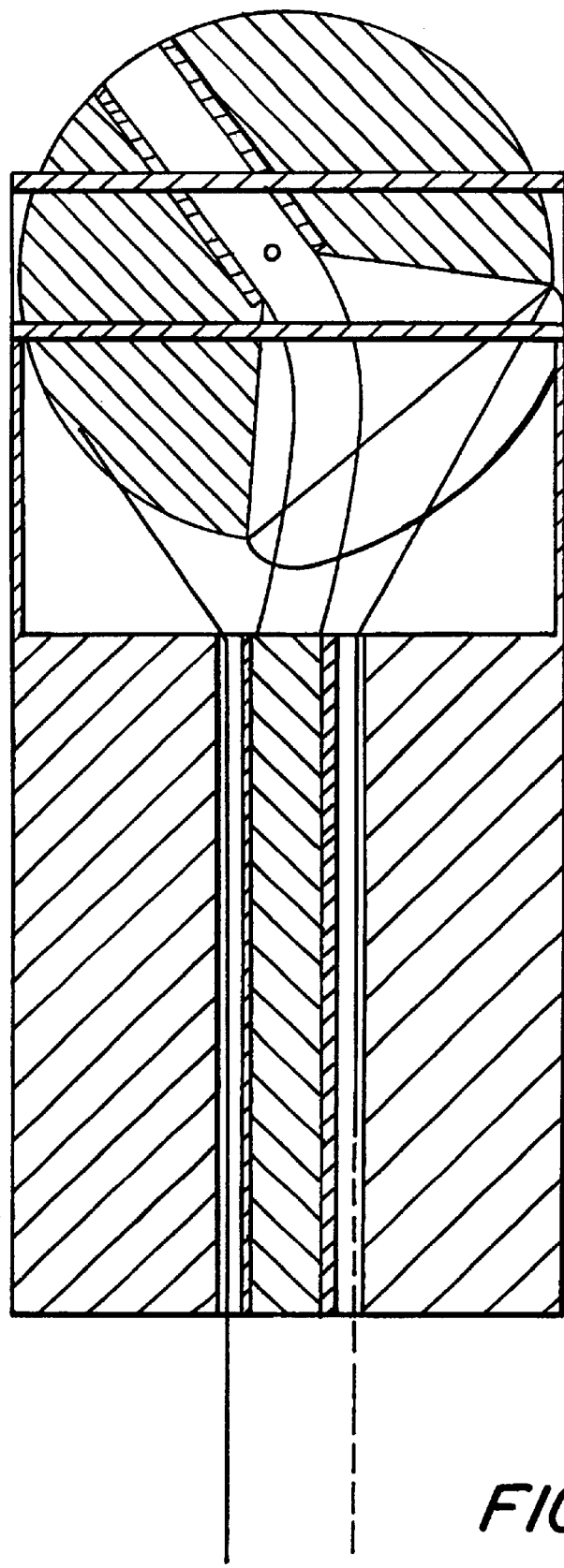
FIG. 4 is a diagram of a node unit as in FIG. 3 showing the tool port in a rotated configuration.

FIG. 4 shows an embodiment of the node as in FIG. 3, with the tool port oriented at an angle. The control system, to be described, should be equipped or preprogrammed so that when the control lines are pulled to the extent that the node reaches maximum rotation an automatic stop is reached such that the operator cannot cause overrotation of the node. Once the desired angle is reached, the control lines can be locked in place, so that the tool can be operated without undesired movement of the node. Such a locking mechanism can be positioned at the brace, 110, or at any point along the control line shaft, 107.

Figure 5:
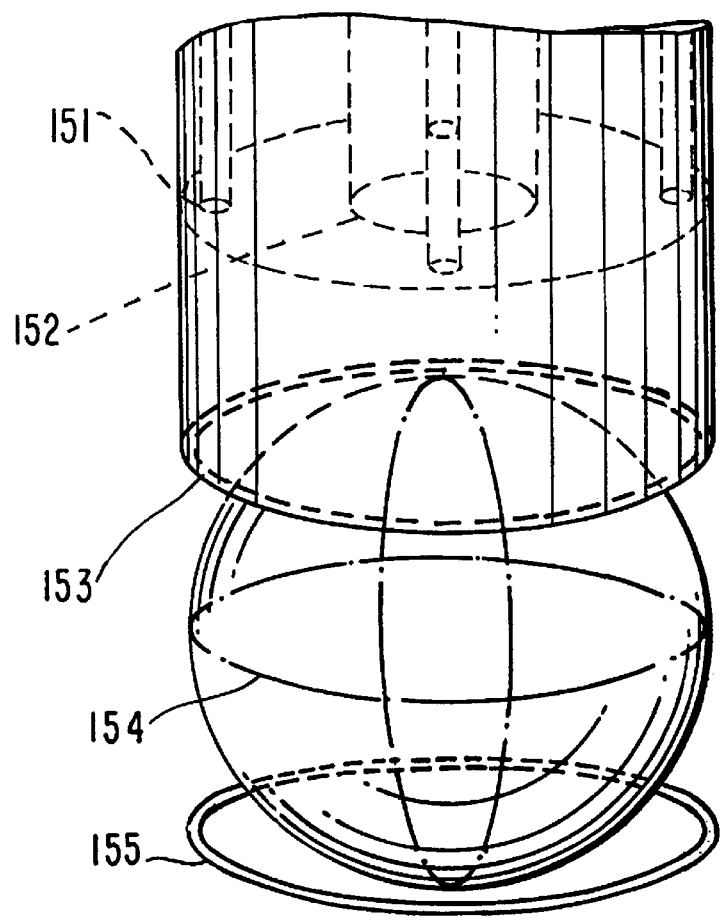
FIG. 5 is a diagram of the node/shaft assembly.

FIG. 5 shows a disassembled node element, with a node, 154, two braces, 153 and 155, and shafts for the tool, 152, and the control lines, 151. The radius of the node ball 154 should be smaller than the inside radius of the shaft 151, and the two braces should be set at positions above and below the center of the node, having internal radii corresponding to the circumference of the node at that point.

Figure 6:
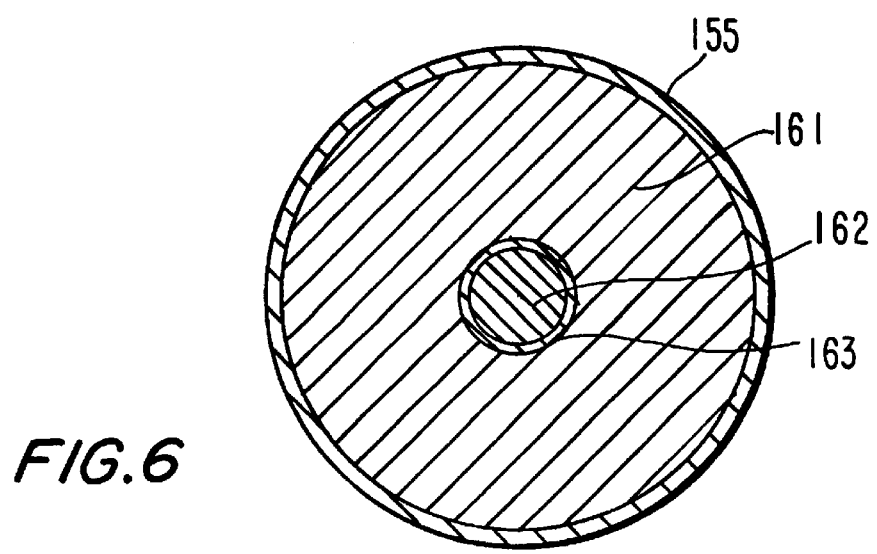
FIG. 6 is a front view of an individual node.

FIG. 6 shows a front view of the node showing the outer brace, 155, the node, 161, the tool brace, 163, and the tool port, 162.

Figure 7:
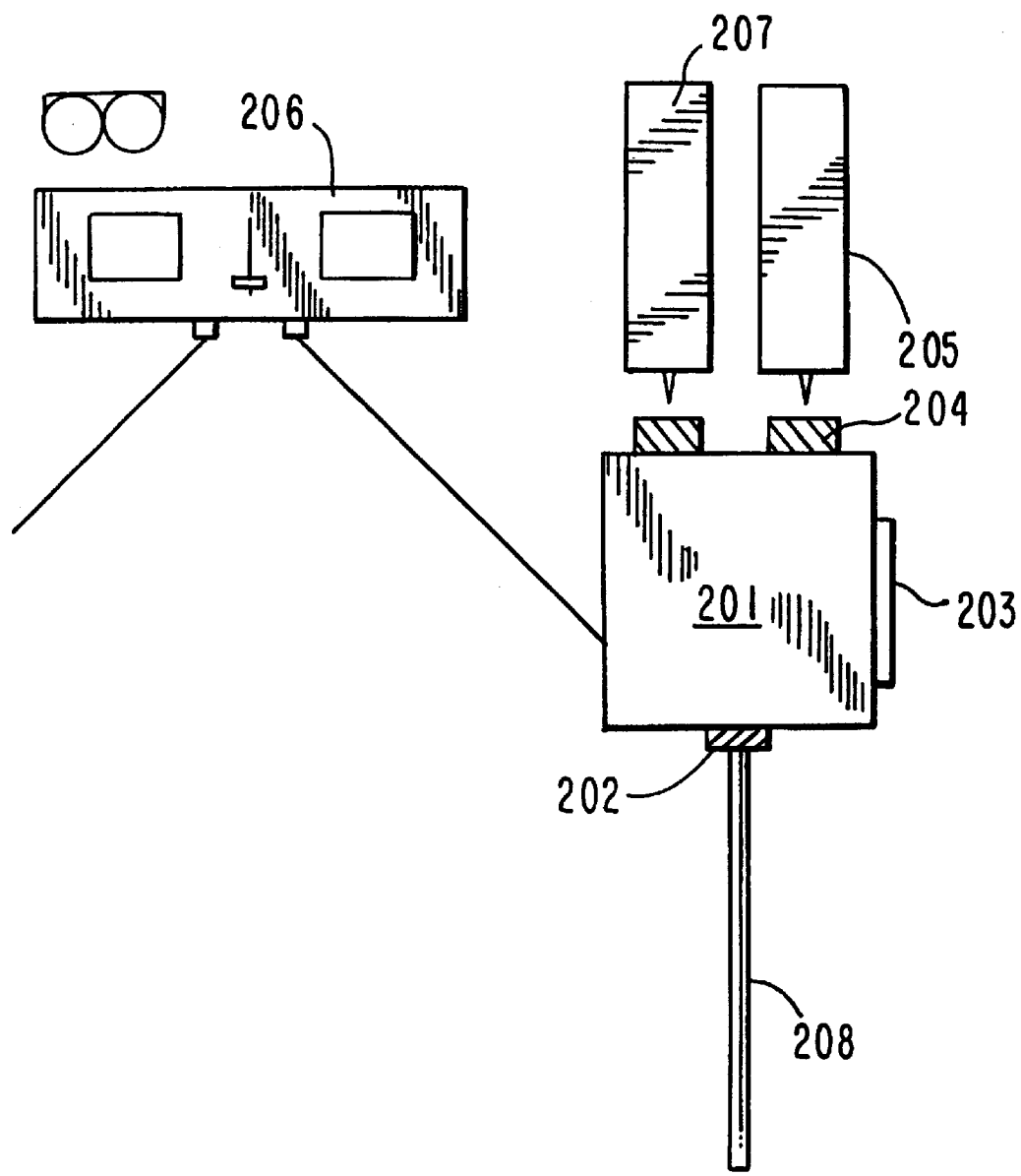
FIG. 7 is a layout of an interface between an operator and a preferred embodiment of the invention.

FIG. 7 is a diagram for a control system that may be used in carrying out and using the invention. The proximal end of the endoscopic surgery tool, 208, is connected to an interface unit, 201, through a port, 202.

On the exterior of the interface unit, ports are located, 203, for connection of power, irrigation, $CO_2$, light, suction or any other desired feature. The interface box is connected to the control unit, 206, which may include viewing goggles, tool controls, and controls for light, suction, irrigation or other function depending on the surgery to be performed. By properly configuring the control panel, multiple endoscopic surgery devices according to the invention can be simultaneously operated.

A control panel may be used, which consists of a substantially flat working surface which measures mechanical displacement, lateral, vertical, depth, and rotation for each of the surface control instruments. The forceps, clip-applier and scissors would also include open/close control as a continuous variable with appropriate tactile feedback.

In use, the gross device housing may be inserted via trocar having a control housing secured on the outside thereof for gross movement and rotation of the entire device. This may be controlled by a separate mechanism, such as a throttle-like shaft on the control panel with a round top which can be rotated approximately 45 degrees for corresponding rotation and advancement/withdrawal of the entire device. Human control is also possible.

On the shaft of the primary dissecting tool on the control panel are other controls for controlling cautery, $CO_2$, and surface irrigation, etc. In one possible configuration, the cautery is controlled by the index finger, the other two by the ring finger.

In the preferred orientation, the surface of the control panel has a group of familiar surgical tools projecting from it at comfortable positions and angles for normal left and right-handed operation. In the center is the primary dissecting/cautery wand which is similar to a hand-held electrocautery wand ready to be grasped like a pen. Further to the right are two other instruments—scissors of the Castro-Viejo type, and a cylindrical shaft with two buttons for suction and irrigation of the field.

For example, each of the tools may assume a resting position flush with the end of the dissector. Therefore, the first motion for the use of each is to push it into the working surface. Like reaching in or out with any instrument, this motion advances the corresponding tool at the working end proportionately. Since the scissors and suction/irrigator share a common shaft housing, only one of these tools can be used at a time. A clip-applying tool shares this same channel.

Any of the above control functions can be substituted, or supplemented by a voice recognition system using available software.

Because the link between the surgeon and the device is electronic instead of mechanical, the distance between the two can be quite remote. This might prove particularly advantageous in a setting where the patient was at high risk for infection or the surgical team may be at risk because of the patient, such as one with HIV disease. Because of the electronic connection, there can also be multiple video and control circuits to allow for control and supervision in a training situation. CD-ROM interactive teaching materials could be readily devised and implemented for learning how to use these devices. A remote expert in a specific procedure could view the procedure remotely and provide advice/instructions to a primary surgeon during the procedure.

Any number of automatic procedures can be implemented, such as a signal when blood pressure, temperature or other parameter exceeds or falls below a certain value. The device could be programmed to automatically deflate a baloon to permit blood flow if the blood pressure exceeded a safe range. The display can show any desired information graphacally or audibly, such as by a graphical overlay of time, pulse, blood pressure, temperature, brain functions, or other vital signs or data.

One benefit of the device is that it can be configured to allow the remote manipulation of surgical instruments using electronic linkages which provide stereoscopic visual and tactile control. This allows the surgeon to use the same sensory feedback mechanisms normally used with open procedures and direct hands-on instruments. Tactile feedback can be provided by a system of transducing the tissue resistance of each instrument (using pressure-sensitive materials) into current which in turn regulates a set of electromagnetic resistors in the shafts of the control instruments providing variable resistance to motion in all three dimensions. This provides the surgeon with the feel of the tissue which is being dissected, grasped, or cut, depending on which of the dissector's tools is being used.

When it is desired to provide tactile resistance to the user, one or more of the control cables is fitted with a tension detector, as shown in FIG. 13. As depicted, the cable from the node (or tool if appropriate) is attached to connector 408. The cable from the controller is attached to connector 410. A spring or other flexible material, 412, is selected so that the electrical resistance varies with tension in the range to be expected during normal surgical procedures. Electrical connectors 404 and 406 create a circuit through the outer surface 401/402, whereby the electrical resistance of the material, 412, can be measured. The material 412 can be any material that undergoes sufficient change of electrical resistance with change in tension to provide a meaningful measurement of tension. The measured change in resistance is recorded by the controller, where it is converted into a corresponding tactile resistance to the surgeon. The proper relationship between resistance at the tool/node level and resistance of the operator level must be determined empirically depending on the size of the tool and node, and the function to be provided by the tool.

Figure 8:
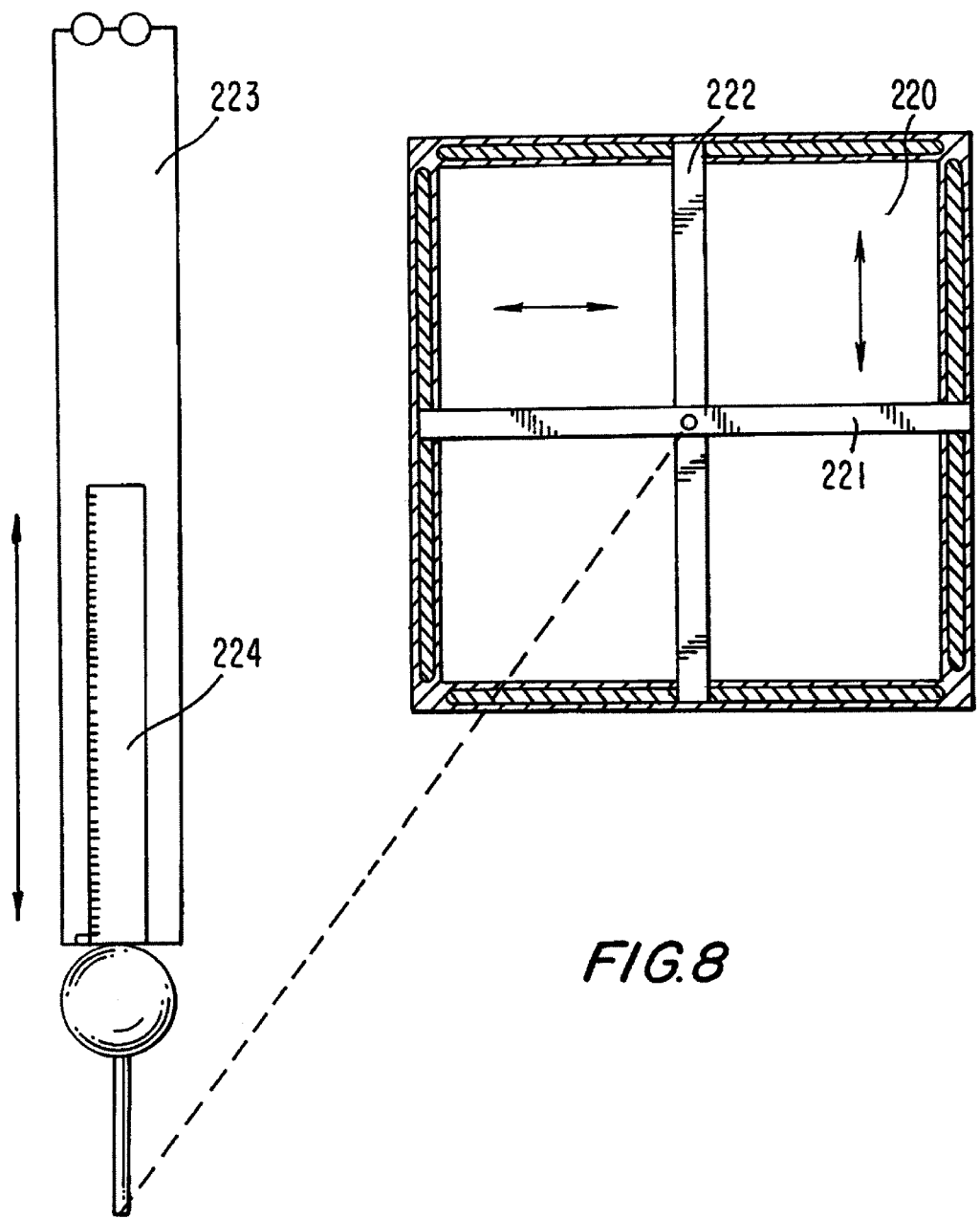
FIG. 8 shows an individual pen unit specifically designed for advantageous use with the device of the invention.

FIG. 8 shows a pen unit designed for use with the surgery device. A control pad, 220, is equipped to sense motion in the (X) and (Y) coordinates, 221 and 222. The pen, 223, can be equipped with controls to move the tool in the (Z) coordinate, 224, or to cause activation of the tool.

Figure 9:
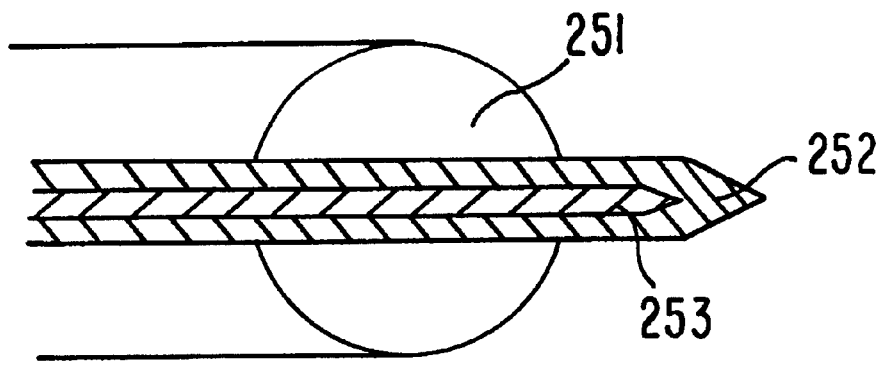
FIG. 9 shows a cautery tool unit specifically designed for advantageous use with the device of the invention.
Figure 10:
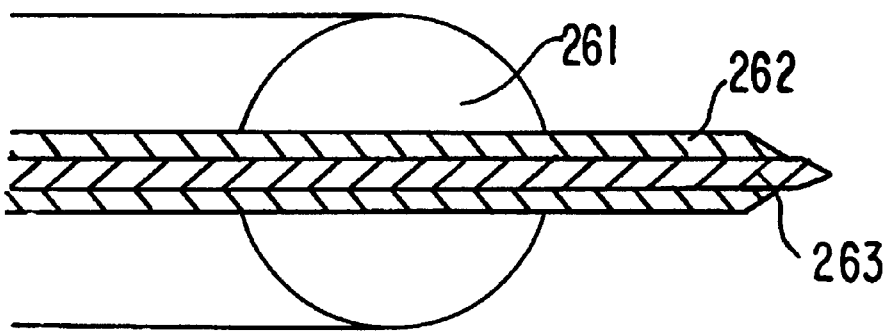
FIG. 10 shows a cautery tool as in FIG. 9 with the cautery pin extended.

FIG. 9 and FIG. 10 show a cautery tool designed for use with the surgery device, shown in the closed and open positions, respectively. A metal pin, 253, is enclosed with a protective sheath, 252, which is inserted through the tool port of a node unit, 251.

To use the tool, the active pin, 263, is extended from the sheath, 262, and pin can be directed to coagulate the target tissue.

Figure 11:
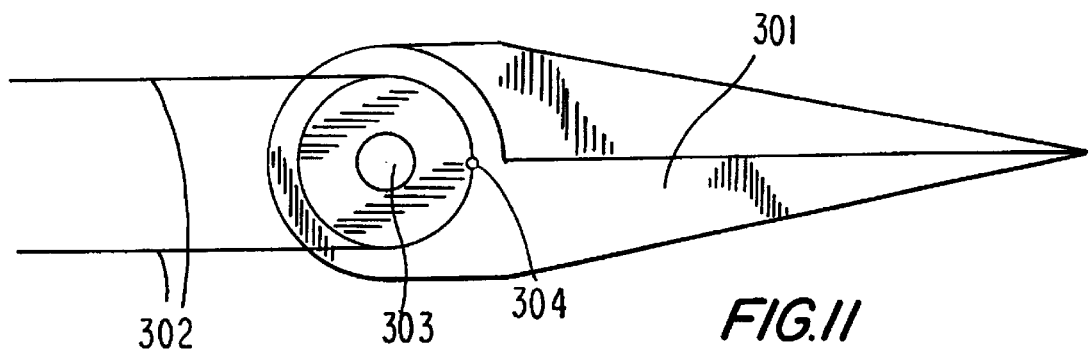
FIG. 11 shows a shear unit specifically designed for advantageous use with the device of the invention.

FIG. 11 shows a surgical shear designed for use with the endoscopic surgery device. The blades, 301, are opened or closed by the control of tension on control lines, 302, about a fixed axis of rotation, 303.

Figure 12:
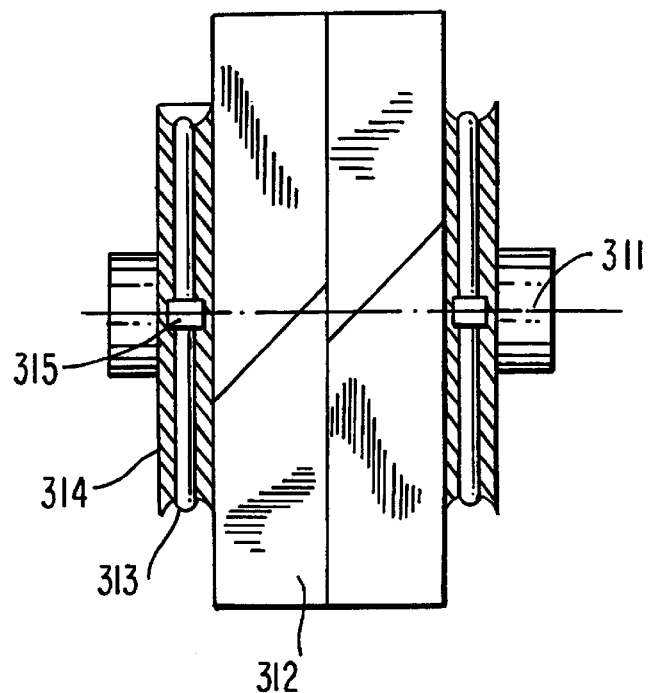
FIG. 12 shows a front view of the shear unit as shown in FIG. 11.

FIG. 12 shows a front view of the same device shown in FIG. 11, depicting the blades, 312, the axis of rotation, 311, the control lines, 313, enclosed with a guide path, 314, and the connection of the control lines to the body of the shear, 315.

Figure 14:
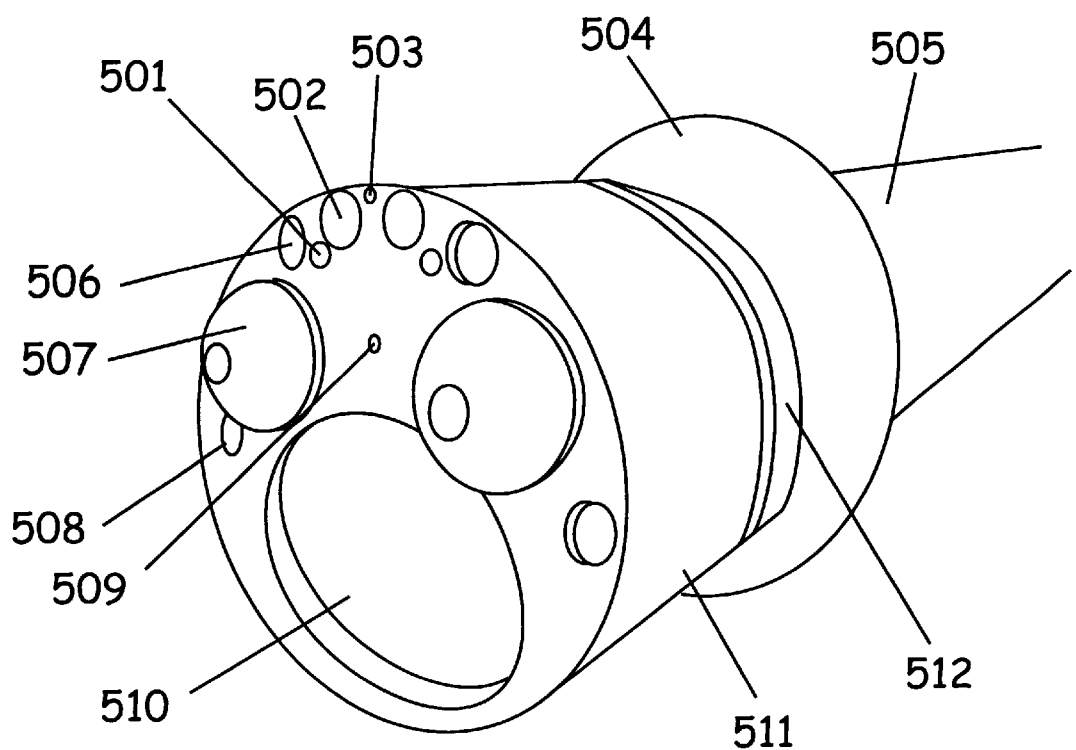
FIG. 14 shows an embodiment of the device specifically configured for endovascular surgery.

FIG. 14 shows an embodiment of the device configured for endarterectomy. RGB chip cameras, 502 are spaced to the right and left of the center axis. Light or other electromagnetic radiation is provided through fiberoptic lines, 506, 508. Two nodes, 507, are spaced to the right and left. Sources for irrigating fluid and gas are placed at appropriate locations, 501. An occluding balloon 404 is attached to the outer shaft 505, and the inner catheter 511 is moveable relative to the outer shaft so that when the balloon is inflated and the location fixed, the shaft and tools can be moved for plaque removal. A relatively large central chamber, 510, preferably with mechanisms for suction and clamping (not shown), is provided for removal of plaque. A small incision is made in the body to gain access to an appropriate artery for insertion of the device. The appropriate artery should be selected taking into consideration the size of the artery, the path to the target area, and the impact on circulatory functions. In many instances the incision will be made in the groin area to gain access to the common femoral artery. This is a procedure that may be done relatively easily under local anesthesia if the circumstances permit.

After gaining proximal and distal control of the artery, vascular clamps are placed to temporarily occlude the blood flow. An incision is made in the wall of the artery, and the device is inserted into the selected artery until the distal end of the device reaches the target area. The device is inserted through the arteriotomy into the lumen. A proximal shaft balloon occluder, 504, is positioned inside the vessel and expanded appropriately to seal the artery around the device. The appropriate clamp is then removed and the device gently advanced into the artery. A guide wire can be passed ahead of the device, either through the central chamber 510, if the artery is not completely occluded. An additional port, 503, may be provided for a needle that can penetrate the plaque and inject $CO_2$, (or other gas or fluid) into the space between the plaque and the artery wall to loosen the plaque which can then be drawn in through suction from the mouth. A port 509 may also be provided for a pressure guage or other instrumentation. Fluoroscopy can also be used to follow the progress and check on position of the device.

Figure 15:
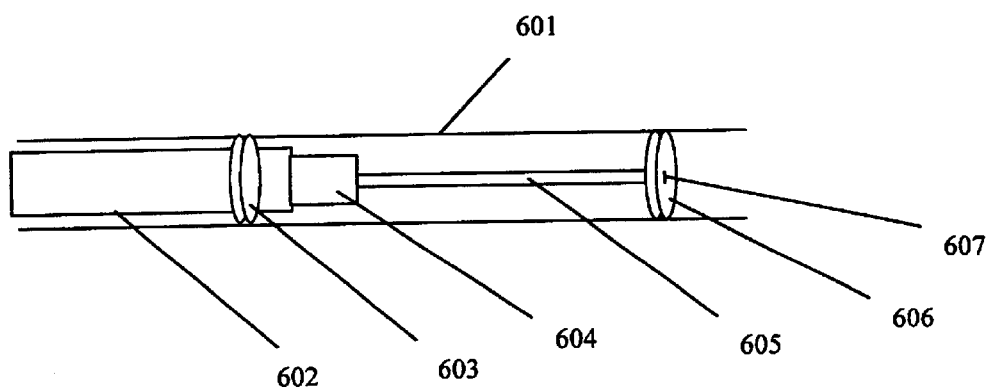
FIG. 15 shows a diagram of a device specifically configured for endovascular surgery, within an artery.

Once the target area is reached, a distal balloon catheter is advanced over the guide wire several cm ahead of the tip of the device and gently inflated. FIG. 15 shows a basic diagram of the device with the distal balloon inflated. The outer shaft, 602 is positioned within the artery, 601. The proximal balloon is inflated, 603, and a shaft 605, is extended to the desired distance, and the distal balloon 606 inflated. Optionally, the balloon may be extended on an internal lumen, (i.e. 605 may be hollow) with an opening provided at the end of the lumen, 607, so that when both balloons are inflated, perfusion of blood can occur through the lumen to be exhausted outside the proximal balloon (or vice versa if operated "upstream"), easing the increase in blood pressure upstream from the device, and providing some blood flow to the tissues downstream from the device. Such a configuration could allow for longer periods of occlusion. A pressure transducer in the device can detect full occlusion by the drop in pressure. Once the segment is occluded, the field is ideally irrigated with physiologic clear fluid to allow visible light spectrum view of the vessel. Alternatively the device can be configured with instrumentation that permits adequate visualization in a blood environment, e.g. x-ray, or other selected electromagnetic radiation, ultrasound, etc. The inner shaft, 604 can be manipulated in and out as well as rotated to give fill view of the internal circumference. The diseased area is identified and grasped with a grasping instrument. The dissecting instrument is then gently manipulated under the intimal plaque to begin the endarterectomy. When the appropriate plane is identified the device is rotated so as to liberate the intima circumferentially. The specimen is then grasped by a grasping instrument within the central core channel. Any number of devices may be provided within the central channel to break up the plaque, if desired, so that it can be removed by suction. The endarterectomy is carried forward by progressive liberation of the plaque by the dissector tool as the device itself is slowly advanced to the point where the distal balloon is encountered. If additional plaque requires removal, the balloon is temporarily deflated, the guide wire and balloon advanced further, and the process repeated except for the fact that the specimen may be already grasped. When the end of the plaque is encountered, it is gently pulled off the normal intima to allow "feathering" of the endpoint. The entire specimen is pulled out through the shaft or at least well into it to avoid embolization. The field is irrigated clean and inspected before withdrawal of the device. The distal balloon is deflated first to allow brief flushing of the field, then the proximal balloon is deflated as the device is removed from the artery. A brief flush is allowed and then the artery is clamped. The arteriotomy is closed in standard fashion as is the wound. If the circumstances permit, the operation should be able to be completed with sufficiently brief blood occlusion that the circulatory functions both locally and generally are sufficient to prevent any lasting adverse effects.

If the target artery is the carotid, fluoroscopic or other guidance may be used to get from the femoral artery to the arch of the aorta and into the origin of the proper vessel. An additional collar balloon may be inflated initially to test back pressure and observe neurologic status in the patient who may be awake. The distal balloon is then advanced gently through the diseased vessel into the internal carotid artery and inflated. An additional balloon may be used to occlude the external carotid. The dissection tool and grasping tool are then employed to begin the endarterectomy at a convenient spot. The specimen is pulled into the shaft with the main core grasper and the dissection proceeds distally into the internal carotid. A short segment of the external carotid maybe included by appropriate mobilization of the plaque around the the origin of this vessel. Great care should be taken to "feather" the distal end of the specimen. The specimen may be withdrawn and the field irrigated and inspected. The distal balloon may be deflated if necessary to allow back bleeding followed by re-inflation and further irrigation to make sure there is no free-floating debris. If so, these remnants may be grasped and sucked into the main channel. The proximal balloon may be similarly deflated briefly and the same type of reinspection carried out. Finally, when the clean field has been assured, all balloons may then be deflated and the device withdrawn all the way.

Another embodiment of this device can be designed for endovascular surgical procedures other than endarterectomy. This would include the concept of direct suturing or otherwise fastening in place an endovascular prosthetic graft for the treatment of aneurysmal disease. It would include the direct visualization and instrumentation for the closure of an atrial septal defect (via a transvenous route) or resection of abnormal muscle from the left ventricular outflow tract (via a transarterial route). Other intracardiac procedures could conceivably be done with the remote intravascular surgical device. This device could have a third node to allow additional instrumentation for cutting, clipping, suturing, or otherwise manipulating tissue. If passed through a small port in the left chest, access to the left atrial appendage could allow the device to be passed directly into the left atrium for repair procedures on the mitral valve. Alternative approaches could be used to other cardiac valves. This would include, but not be limited to procedures currently done by "port-access" on cardiopulmonary bypass. This tool would provide much improved visibility and allow the surgeon to work in the bottom of a small hole with much greater accuracy.

Figure 16:
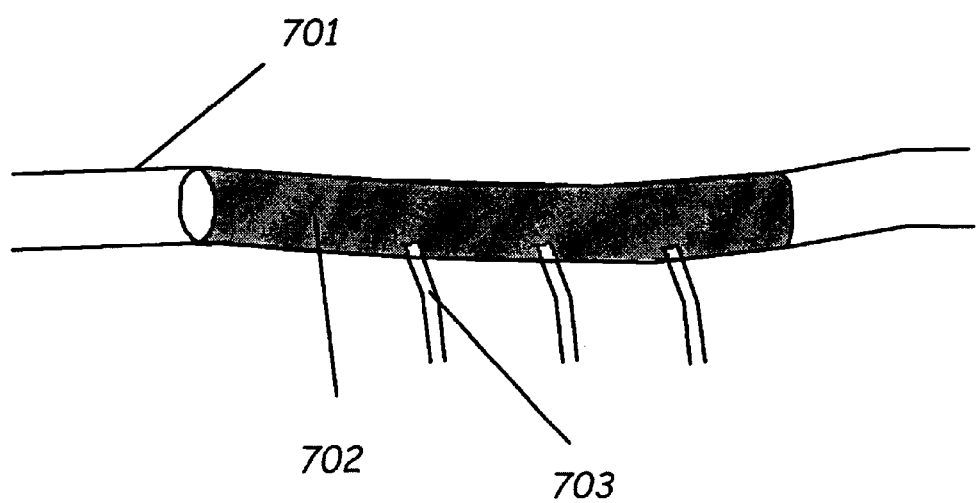
FIG. 16 shows an intraluminally deployed device deployed in an artery.

Another particularly advantageous use of the present invention is in vision assisted deployment of intraluminally deployed devices, such as stents, grafts, and/or occluders. In the usual procedure that is now followed, an artificial graft is first deployed over a desired area of artery, such as a herniated area or area in danger of aneurism. The graft is deployed in a compact form, similar to a rolled up newspaper. A balloon is then inflated inside the graft to expand it to the size of the artery, and a fire locks it in place. A similar procedure is used for stents. With grafts, however, there are frequently other blood vessels that feed into the area that is to be grafted, which can then cause back-bleeding into the area between the graft and the outer artery wall, causing complications. A deployed graft is shown in FIG. 16. The graft, 702 is deployed within artery 701, covering blood vessels 703.

The present invention can be used to plug the undesired blood vessels by deploying first a small balloon or other occluder that is preferable biodissolvable, a short distance into the vessel. Glue is then injected into the opening of the vessel to harden. The occluder then can dissolve leaving the artery blocked, preventing backbleeding once a graft is depolyed. Additional glue can then be injected between the graft and the artery wall to secure the graft. If necessary, one or more holes can then be made in the graft if access to certain arteries is desired. Biological glues are available that have a drying time of approximately 2 minutes. A procedure that would be followed to insert an intraluminal device into an artery (or vein) using the invention and method of the present invention comprises the following steps: (1) an occluder, which is preferably biodissolvable and may be a balloon, is inserted a short distance into each blood vesel to be blocked, and the blood flow is occluded; (2) glue is injected from a device according to the present invention into the area between the mouth of the blood vessel and the occluder; (3) the intraluminal device is deployed and expanded, optionally using a balloon to ensure fill expansion; (4) glue is injected between the intraluminal device and the artery (or vein) wall; this step may occur before the intraluminal device is fully expanded; (5) if desired, cut or puncture holes in the device to allow blood flow from desired blood verssels.

Figure 17A:
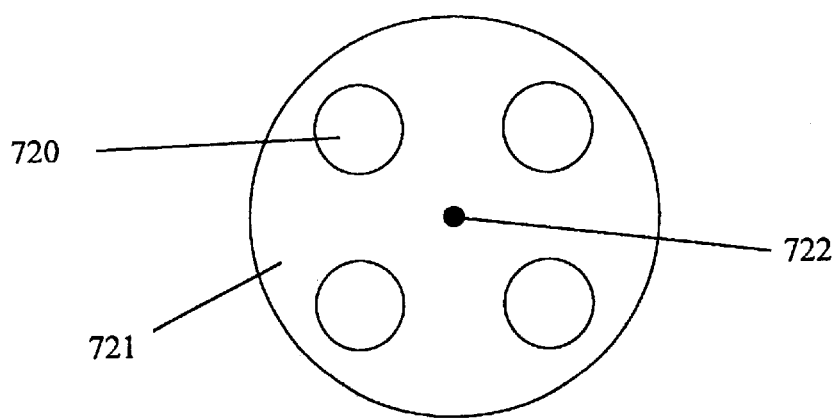
FIG. 17A shows a tool changer.
Figure 17B:
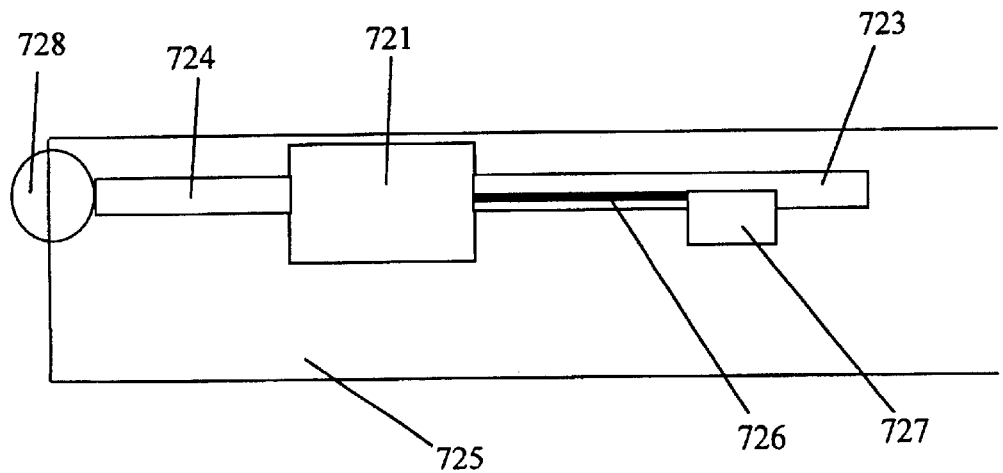
FIG. 17B shows a tool changer within a catheter for changing tools without requiring withdrawl of the catheter from the body.

FIG. 17A and 17B show an example of a tool changer that can be used with the device to allow tools to be changed without withdrawl of the device from the patient. A cartridge, 720, holding a plurality of tools in ports 720, is movably fixed about a rotational shaft, 722, within the outer catheter, 725. In use, the tool would be withdrawn from the node, 728 through the initial shaft 724, and the cartridge, 721, until the tool lies within one of the chambers 720, and the tool shaft is flush with the end of the proximal shaft 723. The tool is then disconnected from its shaft. The cartridge is then rotated about a shaft 726, by a motor 727. Other methods for rotating the cartridge could be used, such as a direct drive motor using gear-type notches on the outside of the cartridge, or a belt drive. The devices are fixed using all necessary supports. When the chamber containing the desired tool is aligned with the shaft, the rotation is stopped, and the tool is connected to the shaft. The tool may then be reinserted through the node and used. The cartridge may be of the appropriate size and shape, and a plurality of tool shafts arranged so that a single cartridge can provide access to a plurality of shafts and/or nodes.

We claim:

1. An instrument comprising a node rotatably mounted within a restraining structure at the distal end of a shaft, wherein a surgical tool extends from the node and the node can be rotated allowing manipulation and orientation of the surgical tool at the distal end of the shaft through control remote from the distal end of the shaft, and comprising a channel for the removal of plaque from a blood vessel, and at least one camera, and further comprising a tool for removal of plaque from a blood vessel.

2. An instrument as in claim 1 wherein said node comprises a substantially spherical ball having an opening therethrough large enough to permit the insertion of a surgical tool wherein the orientation of the node can be controlled using a plurality of lines located at positions which allow rotation of the node in both (X) and (Y) coordinates.

3. An instrument as in claim 1 further comprising an additional second node, and a source of light or other electromagnetic radiation positioned at the distal end of the shaft, configured so that the surgical tool can be operated within the field of an image converted to an operator.

4. An instrument comprising:
   (i) a node at the distal end of a first shaft, wherein a surgical tool can be inserted through the node allowing manipulation and orientation of the tool at the distal end of the first shaft through control remote from the distal end of the first shaft;
   (ii) a plurality of cameras located at the distal end of the first shaft positioned so that they can convey a stereoscopic image to an operator;
   (iii) a source of light or other electromagnetic radiation; and
   (iv) an inner second shaft connected to a balloon, which inner second shaft is extendable relative to the first shaft.

5. An instrument as in claim 4 further comprising an additional second node.

6. An instrument as in claim 4 further comprising a port for the delivery of fluid to the distal end of said shaft.

7. An instrument as in claim 4 further comprising a second balloon located about or before the distal end of said first shaft.

8. A device as in claim 7 further comprising a pressure transducer that measures the difference in pressure caused by the inflation of the first and second balloons.

9. An instrument as in claim 4 wherein said shaft is flexible, and wherein the position of the distal end of the shaft can be oriented by the control of wires within the shaft which are capable of causing the shaft to bend.

10. An instrument as in claim 4 further comprising (a) additional tools stored within said shaft and (b) a changer to allow the substitution of different tools without requiring access to the distal end of the shaft or withdrawal of the tools from the shaft.

11. A device as in claim 4 further comprising a second node, a source for irrigating fluid, and a channel that includes a mechanism for suction.

12. A device as in claim 11 further comprising a third shaft extendable relative to the first shaft, which third shaft is connected to a surgical tool.

13. A method of removing plaque from the inside of a segment of a blood vessel, the method comprising:
   i. making an opening in a blood vessel in a suitable location such that said segment is accessable by the distal end of an instrument as in claim 1;
   ii. inserting a said instrument through said opening until the distal end reaches said segment;
   iii. inflating a balloon attached to the distal end of said shaft to temporarily fix the position of the distal end of the shaft relative to said segment;
   iv. inflating a second balloon attached to a guide wire extending from the distal end of the shaft;
   v. extending one or more tools relative to the distal end of said shaft to liberate plaque
   vi. removing liberated plaque into the shaft.

14. An instrument comprising a node at the distal end of a shaft, wherein a surgical tool can be inserted through the node and the node can be rotated allowing manipulation and orientation of the surgical tool at the distal end of the shaft through control remote from the distal end of the shaft, and comprising a channel for the deployment of an intraluminally deployed device, and including at least one intraluminally deployed device.

15. An instrument as in claim 14 and further comprising a balloon configured to expand the intraluminally deployed device.

16. An instrument as in claim 14 wherein said tool is capable of creating a hole in the intraluminally deployed device.

17. An instrument an in claim 14 further comprising a plurality of cameras for providing a stereoscopic image.

18. A method of deploying an intraluminally deployed device and reducing the risk of backbleeding, said method comprising:
   i. inserting an instrument as in claim 14 into a blood vessel such that the distal end of the shaft is at or near the location where the intraluminally deployed device is to be deployed;
   ii. deploying the device in compact form;
   iii. inflating a balloon within the device to expand it; and
   iv. injecting glue into a blood vessel which presents a risk of backbleeding.

19. The method of claim 18 comprising the further step of introducing glue between the device and the blood vessel.

20. A method of deploying an intraluminally deployed device into a first blood vessel while allowing bloodflow between said first blood vessel and a second blood vessel behind said device after it is depolyed, said method comprising:
   v. inserting an instrument as in claim 15 into the first blood vessel such that the distal end of the shaft is at or near the location where the intraluminally deployed device is to be deployed;
   vi. deploying the device; and
   vii. creating a hole in said device at a location that permits bloodflow between the first blood vessel and the second blood vessel.

21. The method of claim 20 comprising the further step of introducing glue between the device and the blood vessel.

* * * * *